United States Patent
Kochhar et al.

(10) Patent No.: US 6,927,280 B2
(45) Date of Patent: Aug. 9, 2005

(54) COCOA ALBUMIN AND ITS USE IN THE PRODUCTION OF COCOA AND CHOCOLATE FLAVOR

(75) Inventors: Sunil Kochhar, Savigny (CH); Carl Eric Hansen, Epalinges (CH); Marcel Alexandre Juillerat, Lausanne (CH); James McCarthy, Noizay (FR)

(73) Assignee: Nestec S.A., Vevey (CH)

( * ) Notice: Subject to any disclaimer, the term of this patent is extended or adjusted under 35 U.S.C. 154(b) by 24 days.

(21) Appl. No.: 10/442,174

(22) Filed: May 21, 2003

(65) Prior Publication Data

US 2004/0010123 A1 Jan. 15, 2004

Related U.S. Application Data

(63) Continuation of application No. PCT/EP01/13536, filed on Nov. 21, 2001.

(30) Foreign Application Priority Data

Nov. 21, 2000 (EP) .............................................. 00125523

(51) Int. Cl.$^7$ .............................................. C07K 14/00
(52) U.S. Cl. ..................... 530/370; 530/350; 424/185.1
(58) Field of Search ........................ 530/350; 424/185.1

(56) References Cited

FOREIGN PATENT DOCUMENTS

WO    WO 98/45458    10/1998

OTHER PUBLICATIONS

Voigt, J. et al. Food Chemistry 49:173–180 (1994).*
Galau et al., "Cotton Mat5–A (C164) Gene and Mat5–D cDNAs Encoding Methionine–Rich 2S Albumin Storage Proteins", Plant Physiol. 99, 779–782 (1992).
Kochhar et al., "Isolation and Characterization of 2S Cocoa Seed Albumin Storage Polypeptide and the Corresponding cDNA", J. Agric. Food Chem. 49, 4470–4477 (2001).
Yavuz et al., Expression of the major bean proteins from *Theobroma cacao* (cocoa) in the yeasts *Hansenula polymorpha* and *Saccharomyces cerevisiae,* Journal of Biotechnology 46, 43–54 (1996).

* cited by examiner

Primary Examiner—Karen Cochrane Carlson
Assistant Examiner—Anand Desai
(74) Attorney, Agent, or Firm—Winston & Strawn LLP

(57) ABSTRACT

The present invention is directed to a novel 2S cocoa albumin protein that has now been isolated, purified and identified from cocoa beans. The present invention is further directed to flavor precursors generated from the enzymatic hydrolysis of this novel protein and to use of the flavor precursors to form a cocoa flavor useful in making chocolate flavored compositions.

12 Claims, 5 Drawing Sheets

SDS PAGE analysis of different extracts of cocoa acetone powder (CAP) for removal of the 21 kDa albumin.

Tricine-SDS-PAGE analysis of the purified 2S albumin.

PREDICTED α-HELICAL REGIONS AND THE HYDROPHOBICITY PLOT FOR THE *T. cacao* 2S PRECURSOR PROTEIN.

```
1    RPVSKHLDSC CQQLEKLDTP CRCPGLKQAV QQQAEEGEFG REELQEMYET
51   VDKIMNKCDV EPGRCNLQPR NWF (SEQ ID No 4)
```

SCHEMATIC REPRESENTATION OF BRASSICA 2S PROTEIN PROCESSING (A) AND THE PREDICTED PROCESSING SITES FOR THE 2S PROTEIN OF *T. cacao* (B) AS WELL AS THE AMINO ACID SEQUENCE OF THE MATURE POLYPEPTIDE.

COCOA FLAVOUR EVALUATION OF ENZYMATICALLY HYDROLYZED COCOA POLYPEPTIDES.

SEQUENCE LISTING

<160> NUMBER OF SEQ ID NOS: 5

<210> SEQ ID NO 1
<211> LENGTH: 150
<212> TYPE: PRT
<213> ORGANISM: Theobroma cacao

<400> SEQUENCE: 1

```
Met Ala Lys Leu Gly Leu Leu Leu Ala Thr Leu Ala Leu Val Leu Phe
1               5                   10                  15

Leu Gly Asn Ala Ser Val Tyr His Thr Thr Val Thr Val Asp Ser Glu
            20                  25                  30

Glu Asn Pro Trp Gly Ser Lys Glu Ser Ser Cys Gln Lys Gln Ile Lys
        35                  40                  45

Lys Gln Asn Tyr Leu Lys His Cys Gln Glu Tyr Met Glu Glu Gln Ser
    50                  55                  60

Arg Gly Ser Gly Ser Ser Ser Arg Glu Arg Tyr Ser Arg Pro Val
65                  70                  75                  80

Ser Lys His Leu Asp Ser Cys Cys Gln Gln Leu Glu Lys Leu Asp Thr
                85                  90                  95

Pro Cys Arg Cys Pro Gly Leu Lys Gln Ala Val Gln Gln Ala Glu
            100                 105                 110

Glu Gly Glu Phe Gly Arg Glu Glu Leu Gln Glu Met Tyr Glu Thr Val
        115                 120                 125

Asp Lys Ile Met Asn Lys Cys Asp Val Glu Pro Gly Arg Cys Asn Leu
```

```
                130              135              140
Gln Pro Arg Asn Trp Phe
145                   150

<210> SEQ ID NO 2
<211> LENGTH: 34
<212> TYPE: PRT
<213> ORGANISM: Theobroma cacao

<400> SEQUENCE: 2

Arg Pro Val Ser Lys His Leu Asp Ser Cys Cys Gln Gln Leu Glu Lys
1               5                   10                  15

Leu Asp Thr Pro Pro Arg Arg Pro Gly Leu Lys Gln Ala Val Gln Gln
            20                  25                  30

Cys Ala

<210> SEQ ID NO 3
<211> LENGTH: 9
<212> TYPE: PRT
<213> ORGANISM: Theobroma cacao
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 3

Ser Lys Glu Xaa Ser Cys Lys Xaa Ile
1               5

<210> SEQ ID NO 4
<211> LENGTH: 73
<212> TYPE: PRT
<213> ORGANISM: Theobroma cacao

<400> SEQUENCE: 4

Arg Pro Val Ser Lys His Leu Asp Ser Cys Cys Gln Gln Leu Glu Lys
1               5                   10                  15

Leu Asp Thr Pro Cys Arg Cys Pro Gly Leu Lys Gln Ala Val Gln Gln
            20                  25                  30

Gln Ala Glu Glu Gly Glu Phe Gly Arg Glu Glu Leu Gln Glu Met Tyr
            35                  40                  45

Glu Thr Val Asp Lys Ile Met Asn Lys Cys Asp Val Glu Pro Gly Arg
    50                  55                  60

Cys Asn Leu Gln Pro Arg Asn Trp Phe
65                  70

<210> SEQ ID NO 5
<211> LENGTH: 718
<212> TYPE: DNA
<213> ORGANISM: Theobroma cacao

<400> SEQUENCE: 5
aagcagtggt aacaacgcag agtacgcggg gaagaaccaa agccttgtca tctaactagc      60
tatatatcta tatccaccat ggcaaagctc ggtctcctcc tagccaccct tgctcttgtt     120
ctcttcctcg gcaatgcctc cgtttaccac accaccgtca cggttgacag cgaggaaaac     180
ccttggggaa gcaaagagag cagctgtcag aagcagataa agaagcaaaa ctacctcaag     240
```

-continued

```
cactgtcagg agtacatgga ggagcagtcc agaggcagcg gcagcagcag cagccgtgag    300
cgctacagcc gccccgtgag caagcaccta gactcctgtt gccagcaact ggagaagctc    360
gatacgccgt gccgttgccc tggtctaaaa caggcagtgc agcaacaggc ggaagaggga    420
gagtttggga gggaagagtt gcaagagatg tatgagacgg ttgacaagat catgaacaag    480
tgtgacgtag agcctggaag gtgtaacttg caacctcgca actggttcta gagagaaaga    540
aagatcagag ctgcctgatc taatgtaaaa caatgactgt aatgtttcac ccatcaactc    600
tggtgttcta actggaggtt tttggggtga ctagaagtac tgataatcca taaataaaag    660
cacattctcg tgtgcggttg cttttgctt caggccaaaa aaaaaaaaaa aaaaaaa       718
```

COCOA ALBUMIN AND ITS USE IN THE PRODUCTION OF COCOA AND CHOCOLATE FLAVOR

CROSS-REFERENCE TO RELATED APPLICATIONS

This application is a continuation of the US national stage designation of International Application PCT/EP01/13536 filed Nov. 21, 2001, which claims priority to European patent application 00125523.1 filed Nov. 21, 2000, the disclosures of both of which are incorporated herein by express reference thereto.

FIELD OF THE INVENTION

The present invention relates to a novel cocoa polypeptide and the nucleic acid sequence encoding it. In particular, the present invention pertains to the use of said polypeptide and/or flavor precursor fragments thereof in the production of chocolate flavor and for use in making chocolate flavored compositions.

BACKGROUND OF THE INVENTION

In processing cocoa beans the generation of the typical cocoa flavor requires two steps, the fermentation step and the roasting step. During fermentation the pulp surrounding the beans is degraded by micro-organisms with the sugars contained in the pulp being essentially transformed to acids. Fermentation also results in a release of peptides exhibiting differing sizes and a generation of a high level of free hydrophobic amino acids. This latter finding led to the hypothesis that proteolysis occurring during fermentation is not due to a random protein hydrolysis but seems to be rather based on the activity of specific endoproteinases.

This specific mixture of peptides and hydrophobic amino acids is deemed to represent cocoa-specific flavor precursors. During the second step of cocoa flavor production, the roasting step, the oligopeptides and amino acids generated at the stage of fermentation obviously undergo a Maillard reaction with reducing sugars present eventually yielding the substances responsible for the cocoa flavor as such.

So far, research has tried to uncover the molecular pathway of producing cocoa flavor precursors in characterizing enzymes involved in said process and the relevant polypeptide (s), from which the peptides and/or free amino acids are produced.

As for the enzymes many different endo-and exoproteinase activities have been found to participate in the production of cocoa flavor precursors, such as an aspartic endoproteinase activity (Voigt et al., J. Plant Physiol. 145 (1995), 299–307), which accumulates with the vicilin-class (7S) globulin during bean ripening or a cysteine endoproteinase activity, which increases during the germination process when degradation of globular storage protein increases during the germination process when degradation of globular storage protein occurs (Biehl et al., Cocoa Research Conference, Salvador, Bahia, Brasil, Nov. 17–23, 1996).

Moreover, a carboxypeptidase activity has been identified which preferentially splits hydrophobic amino acids from the carboxy-terminus of peptides.

Apart from the enzymes also the protein source of the peptides/amino acids seems to be of importance for the generation of cocoa flavor precursors.

During cocoa bean fermentation the percentage reduction of protein concentration observed for vicilin and albumin was 88.8% and 47.4%, respectively (Amin et al. J. Sci. Food Agric. 76 (1998), 123–128). When peptides obtained by proteolysis of the globulin (vicilin) fraction were post-treated with carboxypeptidase, preferentially hydrophobic amino acids were released and a typical cocoa aroma was detected after roasting in the presence of reducing sugars (Voigt et al., Food Chem. 50 (1994), 177–184). Contrary to that, the predominant amino acids released from the albumin-derived peptides were aspartic acid, glutamic acid and asparagine and no cocoa aroma could be detected. It was therefore concluded that cocoa-specific aroma precursors are mainly derived from the vicilin-like globulins of cocoa, which constitute more than 30% of the total protein contents in the mature cocoa seed. Consequently, the mixture of hydrophobic free amino acids and remaining oligopeptides required for the generation of the typical cocoa flavor components seem to be determined by the particular structure of the cocoa vicilin-class globulins.

Although it is known that hydrophobic amino acids are important cocoa flavor precursors, the specific peptides responsible for generating cocoa flavor during roasting remain by and large un-characterized. Consequently, there is a need in the art to provide further structural data of such peptides and of the way they are produced from their original proteinaceous source in order to be capable to use those peptides for the production of a well-balanced cocoa and/or chocolate flavor.

In WO 91/19801 two major cocoa seed storage proteins and the DNA sequences encoding said polypeptides are disclosed. These two proteins exhibit a molecular weight of 47 kDa and 31 kDa, respectively, and seem to be the vicilin polypeptides, which are deemed to be the source of the flavoring peptides creating the characteristic cocoa flavor. Though the polypeptides have recombinantly been provided as such no specific data as to the synthesis of the flavoring peptides have been provided.

Consequently, there is a need for further elucidating the generation of cocoa flavor from the relevant protein material contained in cocoa.

In order to solve the above problem research has naturally focused on the vicilin polypeptides in cocoa beans, since other protein material contained therein was not considered to contribute to the generation of cocoa flavor as such. In contrast to this general belief the present inventors have now surprisingly found that a polypeptide, being a member of the albumin family, also contributes to the characteristic cocoa flavor during fermentation and roasting.

SUMMARY OF THE INVENTION

The present invention is directed to a polypeptide having an amino acid sequence which is identified by SEQ ID NO: 1 and to flavor precursor fragments thereof. Typically the precursor fragments have a chocolate flavor when reacted with a reducing sugar.

The invention further encompasses specific polypeptides having an N-terminus comprising the sequence identified by SEQ ID NO: 2, SEQ ID NO: 3, or SEQ ID NO: 4.

Preferably the polypeptide is a heterodimer consisting of at least one polypeptide identified by SEQ ID NO: 2, SEQ ID NO: 3, or SEQ ID NO: 4.

The invention also encompasses an isolated nucleic acid comprising a sequence as identified by SEQ ID NO: 5 or a fragment thereof. Preferably the fragments thereof encode a polypeptide identified by SEQ ID NO: 2, SEQ ID NO: 3, or SEQ ID NO: 4. In addition, expression vectors containing one or more of the nucleic acids identified herein and cells containing the recombinant nucleic acid or expression vectors are encompassed by the present invention.

The invention further provides a method of preparing a composition with chocolate flavor. The method generally comprises subjecting the polypeptide identified by SEQ ID NO: 1; SEQ ID NO: 2; SEQ ID NO: 3 or SEQ ID NO: 4 to proteolytic degradation by an endopeptidase or in combination with an exopeptidases to obtain flavor precursors, followed reacting the flavor precursors with reducing sugars for a time sufficient to obtain proteins having cocoa/chocolate flavor.

A method of preparing a composition for the treatment of hypertension, mood depression, bacterial infections and a weakened immune condition is also provided. The method comprises obtaining a polypeptide of the invention and adding the polypeptide to a composition in an amount sufficient to treat hypertension, mood depression, bacterial infections and a weakened immune condition.

Still further, the invention encompasses a chocolate flavored composition. The chocolate flavored composition generally contains at least one polypeptide having an amino acid sequence which is identified by SEQ ID NO: 1 or a flavor precursor fragment thereof having a chocolate flavor when reacted with a reducing sugar. Preferably, the composition contains a polypeptide having an N-terminus comprising the sequence identified by SEQ ID NO: 2, SEQ ID NO: 3, or SEQ ID NO: 4.

DETAILED DESCRIPTION OF THE PREFERRED EMBODIMENTS

Figure 1:
FIG. 1 an SDS-PAGE analysis of different extracts of cocoa acetone powder.

The present invention provides a novel polypeptide as identified by SEQ ID NO: 1 or fragments thereof having a N-terminus comprising the amino acid sequences as identified by SEQ ID NO: 2 or 3, and/or heterodimers of said fragments. In a preferred embodiment the mature polypeptide as identified by SEQ ID NO: 4 is provided.

According to another aspect the present invention provides a nucleic acid as identified by SEQ ID NO: 5, or a derivative thereof, encoding any of the above polypeptide (s). The present nucleic acids also comprise DNA molecules that are derived from the nucleic acid identified by SEQ ID NO: 5 by the degeneracy of the genetic code or by substituting one or more bases with the proviso that a polypeptide identified by SEQ ID NO: 1 will be obtained. The present invention also contemplates allelic variations of the nucleic acid indicated.

During the studies leading to the present invention the inventors originally tried to find peptides derived from the vicilin like globulins present in cocoa. To this end, several experiments were carried out on cocoa acetone powder, wherein the 21 kDa albumin polypeptide was selectively removed. After several purification steps a substantially homogeneous protein preparation was found that showed a major band at about 9 kDa and a weak band at about 4 kDa. The protein thus obtained was sequenced and two amino acid sequences were obtained: RPVSK HLDSC CQQLE KLDTP PRRPG LKQAV QQCA; (SEQ. ID. No. 2) and SKEXS CKXI (SEQ. ID. No. 3)

On the basis of these information a cDNA library prepared from T. cacao was screened for nucleic acids encoding such (a) protein (s) and a polypeptide with a theoretical molecular weight of about 17 kDa could be located. The nucleic acid and the deduced amino acid sequence is shown in SEQ ID NO: 5 and SEQ ID NO: 1, respectively.

As may be seen from a comparison of the amino acid sequences obtained from sequencing the purified protein and the amino acid sequence (open reading frame) derived from the nucleic acid both of the sequences are contained in the open reading frame of the subject nucleic acid molecule indicating a post-translational processing of a precursor molecule as represented by the 17 kDa polypeptide.

As is known from other species, e. g. rape seed, a precursor polypeptide of the 2S protein is subjected to different post-translational processing steps including the generation of two subunits that are held together by intra- and inter-chain disulfide bonds. These two peptides are produced by removal of peptides at the N-terminus, between the subunits and at the C-terminus of the precursor molecule. On the basis of the information provided a similar mechanism seems to take place with the 2 S-polypeptide of T. cacao, as evidenced by the occurrence of two different N-terminal sequences.

Consequently, according to a preferred embodiment the present invention provides a polypeptide, which is derived from the 17 kDa polypeptide, and which has a N-terminus comprising the amino acid sequence as identified under SEQ ID NO: 2. This part represents a subunit of the mature 2S-polypeptide.

According to yet another preferred embodiment the present invention relates to a polypeptide derived from the 17 kDa polypeptide as described herein, and which a N-terminus comprising the amino acid sequence as identified under SEQ ID NO: 3. This part of the 17 kDa polypeptide represents another subunit of the mature 2S protein.

Further, it could now be shown that the present 2S protein of T. cacao also yields peptides, which upon reaction with reducing sugars results in cocoa flour products (see below).

Therefore, the present 17 kDa polypeptide or fragment thereof, preferably fragments comprising the amino acid sequence of the subunits of the mature 2S-polypeptide may be recombinantly produced to obtain cocoa flavor precursors which may be used for producing cocoa flavor.

For expression a nucleic acid coding for any of the polypeptides of the present invention may be incorporated in a suitable vector, with which a cell of interest is transformed. Since the polypeptide does not seem to be glycoslated, expression in prokaryotic cells is also possible. To this end, the nucleic acid as identified by SEQ ID NO:5 or a fragment thereof may be incorporated in an expression vector, such as pUC, pNZ 124 (Platteuw et al., (1994) Appl. Env. Microbiol. 60,587), pGK12 (Walker et al., (1996) FEMS Microbiol. 138,233;), or pG+host9 (Maguin et al., (1996) J. Bacteriol 178,93 1). For expression in e.g. methylotrophic yeast Pichia pastors, the vector pPICZaA as described Manual of the Easy Select Pichia Expression kit, version B (Invitrogen, The Netherlands) can be used.

Heterologous expression in YarTowia lipolytica can be obtained with the vector pINA 1294 containing a defective ura3 gene (ura3d4) that allows direct selection for multicopy integrants (Madzak, C., Treton, B. and Blanchin-Roland, S. (2000) J. Microbiol. Biotechnol. 2 (2): 207–216). For Hansenula polymorpha, B 14-derived expression vectors containing the FMD promoter and MOX terminator as described in Mayer, A. F., Heilmuth, K., Schlieker, H., Lopez-Ulibatri, R., Oertel, S., Dahlems, U., Strasser, A. W. M., van Loon, A. P. G. M. (1999) Biotechnol. Bioeng. 63: 373. It will be appreciated that the skilled person is well aware of arranging the corresponding nucleic acid such that an open reading frame is present, such as is e. g. necessary for producing the fragments of the 17 kDa precursor. To this end, a start codon may be positioned directly in front of the respective N-terminus of a fragment or may be positioned such that it is spaced from the polypeptide to be expressed by a linker which may support the isolation of the resulting polypeptide. Methods for introducing a nucleic acid into a vector and for transforming cells with the vector are known to the skilled person and may be found in "Maniatis and Sambrook, A Laboratory Manual, Cold Spring Harbor (1992), USA".

The cell of interest may be any cell or cell line with which the present polypeptide or a fragment thereof may be expressed. Expression in *E. coli* may be advantageous due to its easy handling and the option to choose a variety of different expression vectors for expressing polypeptides within the cell or in secreted form. However, the nucleic acids of the present invention may well be incorporated in cells of higher origin, such as plant cells, in particular in cells of T. cacao. In this respect over-expression of the 2S polypeptide may be achieved in a recombinant T. cacao plant by incorporating a nucleic acid as identified by SEQ ID NO: 5 into a cocoa cell using vectors suitable for plants, such as the Ti-plasmid or using the technique of homologous recombination. Such a plant will eventually yield a higher content of cocoa flavor precursors.

In the case of producing the polypeptides of the present invention by recombinant means in bacteria, yeast or in cell culture in general the polypeptide may be isolated by methods known per se and the purified 2S polypeptide may be subjected to a proteolytic degradation, using the different enzymes known to participate in the generation of cocoa flavor. In a subsequent step the flavor precursors thus obtained may be contacted with sugars such that a Maillard reaction may take place eventually obtaining cocoa/chocolate flavor.

However, substances yielding cocoa flavor are known to also beneficially affect physiological and/or medical conditions, and may thus be used in the treatment of hypertension or mood depression. Also immune modulatory activities are known, such as improving an individuals capability to cope with bacterial challenges. The present invention therefore also envisages such usages.

EXAMPLES

The following examples illustrate the invention in a more detailed manner. It is, however, understood that the present invention is not limited to the examples but is rather embraced by the scope of the appended claims.

Example 1
Identification and Isolation of Cocoa 2S Albumin

Cocoa pods were obtained from experimental farms in Ecuador, Ivory Coast and Malaysia and unless stated otherwise all studies were carried out using West African Amelonado cocoa beans. Due to the high fat and polyphenol contents, proteins were extracted from Cocoa Acetone Powder (CAP). The CAP was prepared from non-defatted cocoa beans as follows: Sun-dried unfermented cocoa beans were passed through a bean crusher followed by a winnower to remove shells. The cocoa nibs were milled and the nib powder was passed through 0.8-mm sieve. The cocoa nib powder was suspended in 80% (v/v) aqueous acetone, stirred and subsequently centrifuged. The residue was extracted 5-times with 80% (v/v) aqueous acetone and 3-times with 100% acetone. The acetone powder was dried under reduced pressure.

CAP (5 g) was suspended in 50 ml ice-cold sodium-acetate buffer (50 mM, pH 4.0) containing 0.1 mM pepstatin. The suspension was sonicated for 2×30 sec with a 10 min layover interval on ice. The suspension was centrifuged at 20,000 g for 15 min at 4 C. The residue was extracted twice with buffer pH 4.0 (supra) followed by water extraction employing sonication. The residue from the water extract was finally extracted with 100 mM Tris-hydrochloride, pH 8.5. The supernatant was passed through a sterile 0.22 urn filter and stored at –20 C.

SDS-PAGE analysis of pH 8.5 extracts following two exhaustive washing of the residue with pH 4 buffer followed by a water wash showed complete absence of the high intensity 21 kDa protein (FIG. 1). Separation was carried out in a conventional manner (Lammli (1970)), employing 12.5% gels. Lane A contains low range molecular markers (Bio-Rad), lane B contains total CAP extract with 1% SDS, lane C contains CAP extracted 2 times with 100 mM acetate buffer, pH 4.0 (supra), lane D contains a subsequent water extract of the residue of lane C and lane D contains an extract of the residue of D with 100 mM Trishydrochloride buffer, pH 8.5.

It could be shown that the 21 kDa protein could be essentially removed. Further under these conditions a protein having a molecular weight of about 9 kDa was detected which was further purified.

Chromatographic steps were performed at room temperature using a BioCad 20 chromatography station (Perseptive Biosystems). The frozen CAP extract was thawed overnight at 4 C and, if necessary, adjusted to pH 8.5 with 1M Tris-chloride buffer, pH 8.5.

The clear CAP extract was applied to a Resource Q column (Amersham-Pharmacia biotech) equilibrated with buffer A (50 mM Tris-bis-propane chloride, pH 8.5) at a flow rate of 5 ml/min. The column was washed with buffer A until A280 decreased to below 0.05. The column was eluted with a linear gradient (20 column volumes) of NaCl 0–500 mM in buffer A. Fractions were analyzed by SDS-PAGE, and those showing the 9 kDa protein were pooled, concentrated by ultra-filtration (PM-10 membrane, Amicon). The concentrated 9 kDa protein fraction was injected onto a HiLoad Superdex 30 column (26×600 mm) equilibrated with 50 mM sodium phosphate buffer, pH 7 containing 100 mM NaCl. The column was eluted with the same buffer and fractions were collected. The fractions showing the 9 kDa protein were pooled and concentrated by ultra-filtration. The purified protein solution was passed through a fast-desalting PD-10 column (Amersham-Pharmacia Biotech) for buffer exchange to water, sterile filtered, and stored at –20 C.

Figure 2:
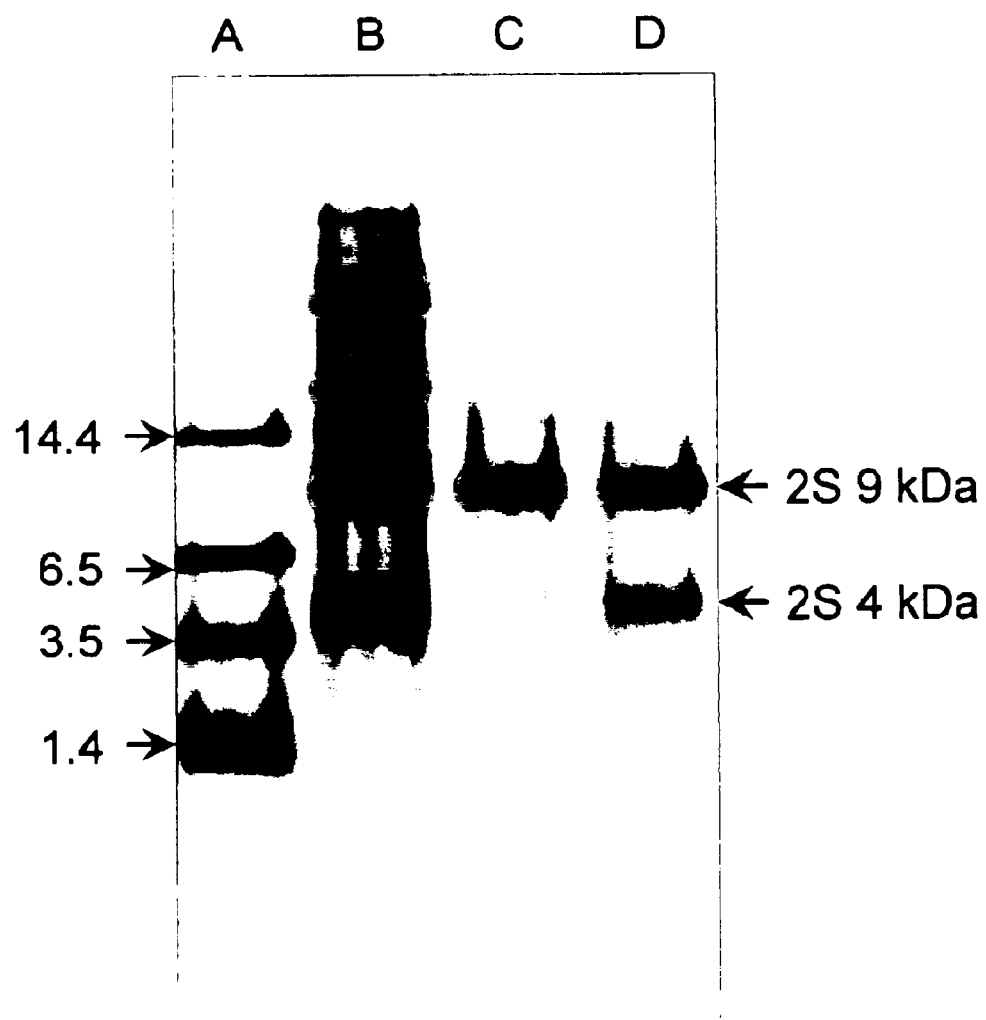
FIG. 2 shows an SDS-PAGE analysis of the purified 2S albumin.
Figure 3:
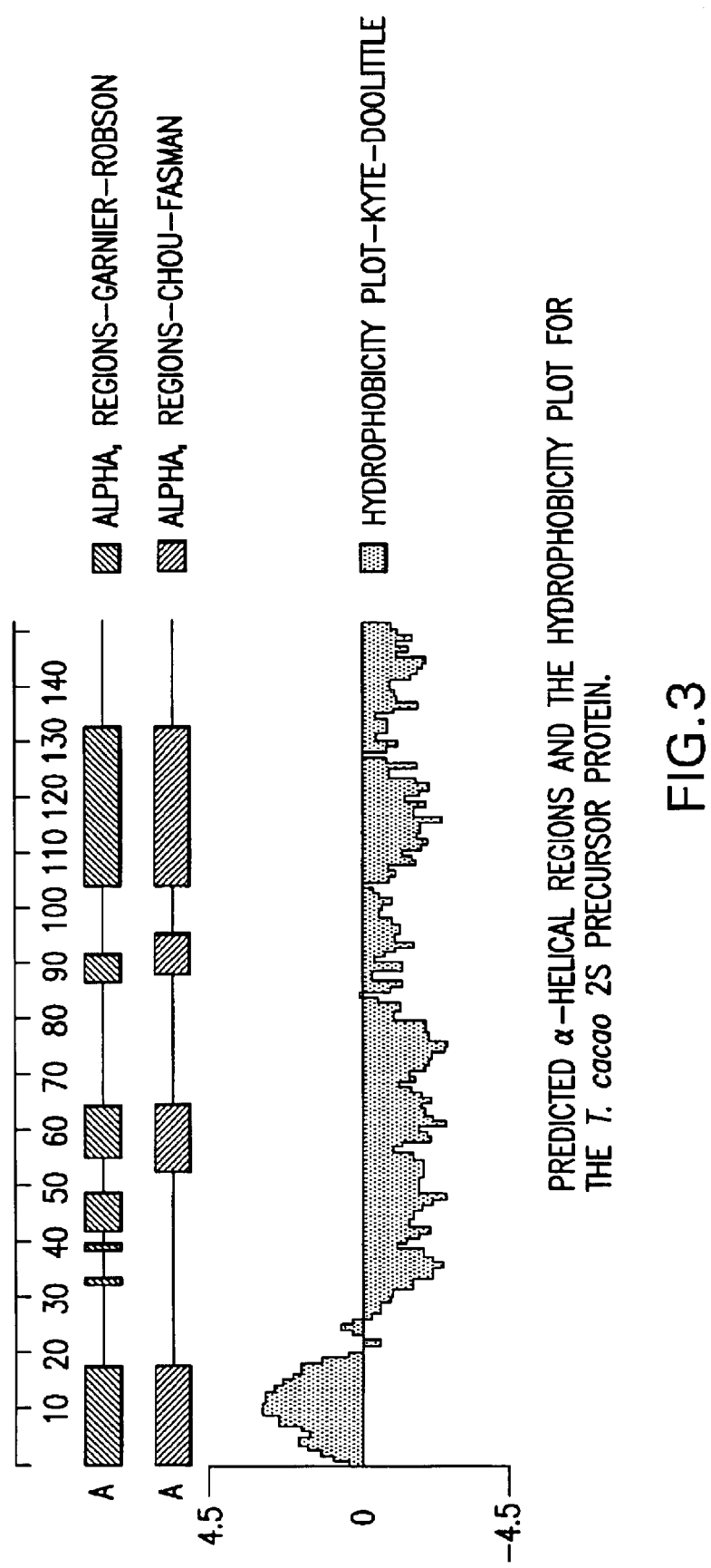
FIG. 3 shows the predicted α-helical regions and the hydrophobicity plot for the T. cacao 2S precursor protein.
Figure 4:
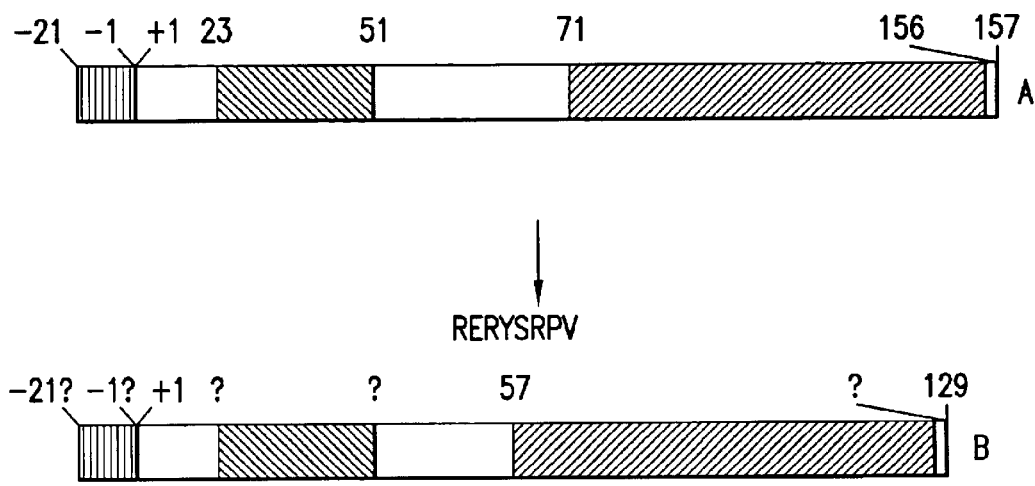
FIG. 4 is a schematic representation of Brassica 2S protein processing (A) and the predicted processing sites for the 2S protein of T. cacao (B) and shows the amino acid sequence of the mature polypeptide (SEQ ID NO:4) according to tryptic peptides mass fingerprints of the purified protein.

Two successive chromatography steps, anion exchange and gel filtration resulted in apparent homogeneity of the protein preparation as judged by SDS/PAGE followed by Coomassie Brilliant Blue staining (FIG. 2). 10 pl samples were diluted 3× with sample buffer in the presence and absence of 13-mercaptoethanol and centrifuged and electrophoresed at 100 V.

The gels were stained for small peptides. Lane A contains a molecular weight marker, lane B contains a CAP extract (1% SDS/50 mM phosphate buffer, pH 7,0) following exhaustive extraction at pH 4 ; lane C purified 2S albumin in the absence of 13-mercaptoethanol, and lane D purified 2S albumin under reducing conditions.

The glycosylation was assessed employing the glycoprotein detection kit from BioRad. The purified cocoa albumin was not found to be glycosylated.

The polypeptide was subjected to Edman degradation resulting in 2 amino acid sequences to be obtained, i.e., RPVSK HLDSC CQQLE KLDTP PRRPG LKQAV QQCA and SKEXS CKXI. SEQ ID NOS: 2 and 3, respectively.

Example 2
Cloning of the 2 S Albumin Gene

Total RNA was isolated from mature and less mature seeds according to methods known per se (Maniatis, supra). Poly A+RNA was prepared from the total cocoa seed RNA using the Oligtex kit from Qiagen following the kit instructions for 250–500 μg total RNA.

The final pellet was resuspended in 10 μL of RNase free water, and the concentration of RNA present was estimated to be approximately 5–10 ng/μL using Clontech nucleic acid "Quick Sticks".

The synthesis of cDNA from the polyA+mRNA was carried out using a SMART PCR cDNA synthesis kit from Clontech. The method used was as described in the kit instructions. For the first strand cDNA synthesis step, 4 μL (20–40 ng) of poly A+mRNA was used and 200 units of Gibco BRL Superscript II MMLV reverse transcriptase. The PCR step of the SMART protocol was also set up as directed in the kit instructions, except only 2 μL of the first strand reaction was added. First, 18 cycles of a PCR were run, then, 35 uL was taken out of the total reaction (100 μL) and this part of the reaction was run for a further 5 cycles of PCR.

A pool of two PCR reactions was then prepared; 40 μL of the 18 cycle PCR reaction and 15 μL of the 23 cycle PCR reaction. 2.5 μL protease K (Boehringer Mannheim, nuclease free, 14 μg/μL) was added to this cDNA mixture and the reaction was carried out at 45° C. for one hour. After a brief spin, the reaction was stopped by heating the mixture to 90° C. for 8 min. The mix was then chilled on ice, and 5 μL of T4 DNA polymerase (New England Biolabs) was added (3 units/μL), and the reaction was incubated at 14–16° C. for 30 min. Then, 25 μL of Milli Q water, 25 μl phenol (Aqua phenol), and 25 μL chloroform/isoamyl alcohol (Ready Red) was added. This mixture was vortexed, spun, and the top aqueous layer was taken. The phenol layer was re-extracted with 50 μL of water. The two resulting aqueous layers were then pooled and re-extracted with chloroform/isoamyl alcohol (Ready Red). The DNA in the aqueous layer obtained was ethanol precipitated as described above. The dried DNA obtained was resuspended in TE buffer (10 mM Tris-HCl pH 8.1 mM EDTA) and its concentration was calculated to be approximately 75 ng/μL using nucleic acid "Quick Sticks" strips from Clontech.

The cDNA was then ligated into the PCR-Script Amp SK (+) cloning vector of Stratagene. Two μL of the ligated DNA was transformed into Stratagene Ultracompetent cells XL-2 Blue as described in the instruction manual for these cells.

Eighteen randomly chosen inserts containing clones of the cDNA library were subjected to a single DNA sequencing run using the T3 primer present in the pPRC-Script Amp vector. Potential protein coding sequences of these DNA sequences were identified using the "Lasergene" suite of DNA analysis programs from DNASTAR Inc. The amino acid sequences obtained for open reading frames were then compared to the sequences obtained in the Edman degradation (example 1, above). For the 18 clones analyzed 3 clones were found to contain the same cDNA sequence encoding a protein harboring the amino acid sequences as identified for the polypeptide searched for.

The DNA insert is 718 base pairs in length and an analysis of the protein encoded by this cDNA shows that the 2S protein is probably produced first as a precursor having 150 amino acids with a calculated molecular weight of 17,125 Da and a pI of 6.15. The amino acid composition profile for the precursor 2S protein shows that the cocoa 2S protein has a relatively high level of sulfur containing amino acids.

Figure 5:
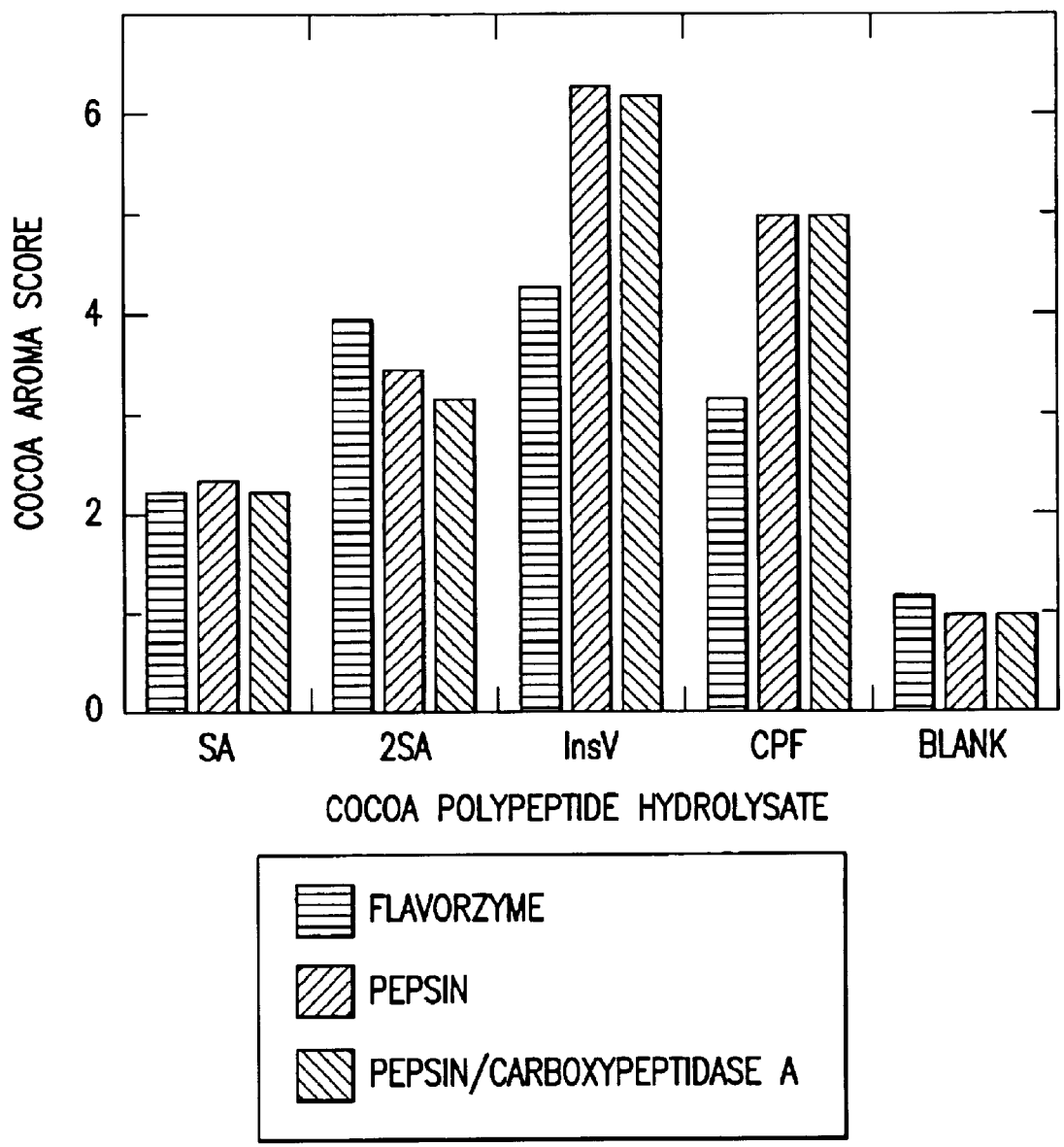
FIG. 5 shows a cocoa flavor evaluation of enzymatically hydrolyzed cocoa polypeptides.

Example 3
Biochemical Characterization of the 2S-Protein
LC/ESI-MS Analysis Data of a Cocoa 2S Albumin:

LC/ESI-MS analysis showed the molecular weight of the mature protein to be 8513±2 Da (FIG. 5). Reduction and S-pyridinylethylation resulted in a positive shift of 630 mass units (Mr 9,145) indicating the presence of 6 cysteine residues.

Tryptic Peptide Mass Fingerprinting:

The primary structure of the mature cocoa 2S albumin having a molecular mass of 8513±2 Da was determined by generating the tryptic peptide mass fingerprints of the reduced and pyridinylethylated albumin by RP-HPLC/ESI-MS. A total of 10 peptide masses were detected (Table 1).

TABLE 1

Tryptic Peptide Analysis of Cocoa 2S Albumin by LC/ESI-MS

| Theoretical average $[M + H]^+$ | Sequence position | Tryptic peptides | Average observed $[M + H]^+$ |
|---|---|---|---|
| 3829.042 | 4–39 | ND | |
| 1576.735 | 105–118 | T8 | 1576.7 |
| 1513.673 | 119–130 | T7 | 1513.6 |
| 1439.568 | 55–65 | ND | |
| 1303.577 | 83–93 | T9 | 1513.5 |
| 836.462 | 76–82 | ND | |
| 775.340 | 135–141 | T3 | 880.4 |
| 730.366 | 142–147 | T5 | |
| 724.322 | 66–73 | ND | 809.4 |
| 704.340 | 94–99 | T6 | |
| 681.287 | 40–45 | ND | |
| 665.362 | 50–54 | ND | 622.3 |
| 517.280 | 100–104 | T4 | 505.3 |
| 505.280 | 131–134 | T2 | |
| 466.208 | 148–150 | ND | |
| 388.255 | 46–48 | ND | |
| 349.190 | 1–3 | ND | |
| 304.162 | 74–75 | T1 | 586.4 |
| 147.113 | 49–49 | T10 | 1536.5/1447.9 |

ND, not detected

The mature 2S protein of plants such as Brassica napus (rape seed) and pumpkin (Hara Nishimura et al., "Proglobulin processing enzyme in vacuoles isolated from developing pumpkin cotyledons", Plant Physiol. 85 (1987) 440-445) are known to be post-translationally processed to generate two subunits. A comparison of the observed tryptic peptide masses of the mature protein against the translated amino acid sequence showed a 100% amino acid sequence match to the residue 78 to 147 (SEQ ID NO: 1). The peptide fragments containing the cysteine residues showed the expected positive mass shift of 105 due to S-pyridinylethylation. Every identified peptide mass was subjected to MS/MS analysis to determine either a complete or partial amino acid sequence to confirm its mapping to the amino acid sequence of the albumin. The C-terminal peptide NWF could not be detected. Also N-terminal peptides (sequence residues 1–77) could not be detected indicating that the 2S cocoa albumin is post-translationally processed to yield a much smaller polypeptide from its N-terminal end.

Hydrophobicity:

Analysis of an hydrophobicity plot for the cocoa 2S precursor protein (SEQ ID NO:1) clearly indicates that the N-terminal region of this 2S protein encodes a distinct short hydrophobic region that is considered to represent the signal peptide sequence. The predicted α-helical regions for the T. cacao 2S precursor shows that the position of the N-terminal residue of large cocoa 2S fragment mapped by N-terminal sequencing (position 77 in SEQ ID NO: 1) has a noticeable absence of α--helical forming sequences.

Example 4

Flavor Potential of the 2S Polypeptide

Isolated cocoa polypeptide fractions (lyophilized powder), namely 21 kDa albumin (SA), 8.5 kDa albumin (2SA), insoluble vicilin protein fraction (InsV) and total polypeptide fraction (CPF) were suspended in 100 mM acetate buffer, pH 5 and digested with 1% (w/w total protein) Flavorzyme for 16–24 h. Alternatively, the polypeptides were digested in 100 mM acetic acid, pH 3 with 1% (w/w protein) porcine pepsin for 16–24 h. Both samples were freeze dried. A subset (at least 70%) of pepsin hydrolyzed sample was further digested with 200 units of carboxypeptidase A. Following analytical analysis (free and total amino groups and amino acids), an identical amount of each hydrolysate was reacted with reducing sugars as described under the following section.

The process reaction flavors using amino acid residues or protein hydrolysates were prepared as follows: The reference model reaction was prepared by reacting 0.8% Leu, 1.45% Phe, 0.8% Val, 1.5% fructose, 1.5% water (4 drops of 50% (w/v) NaOH in 20 ml water) and 94% propylene glycol at 125° C. (temperature of oil bath) for 60 min under reflux. The cocoa protein hydrolysate-based reaction flavors were prepared by replacing the amino acids with 1% (w/w) of lyophilized hydrolysate. At the end of the reaction, each mixture was cooled to room temperature, and its final pH as well as optical density at 420 nm was measured. The reactants were transferred in a dark-brown bottle and stored at 15 C until sensory profiling.

A panel of 8 persons was used to evaluate the flavor (aroma and taste) of the process reaction on a scale of 1–10 for different flavor attributes. Tasting was performed on 0.1% (w/w) solutions in 1% (w/w) sucrose. For each sensory session an average of score data was used to evaluate the flavor potential of the various polypeptide fractions.

The results are summarized in FIG. 5, which shows the evaluation of various precursor pools generated from the enzymatically hydrolyzed cocoa polypeptide fractions in the flavor assay system. As expected the most cocoa flavor is produced by the vicilin storage protein fraction. Surprisingly, also the newly identified 2S albumin showed respectable cocoa flavor when hydrolyzed by Flavorzyme or pepsin/carboxypeptidase combination. Selection of the enzyme cocktail for extensive hydrolysis showed no remarkable difference suggesting that cocoa polypeptides harbor innate amino acid sequences for generation of cocoa flavor. The flavor quality and intensity of 2S albumin was surprisingly superior to the highly abundant 21 kDa cocoa albumin. These data strongly support the notion that 2S polypeptide together with vicilin storage protein contributes significantly to the accumulation of the potential cocoa flavor precursors.

What is claimed is:

1. A polypeptide comprising an amino acid sequence which is identified by SEQ ID NO:1 or a flavor precursor fragment thereof, said flavor precursor fragment having an N-terminus comprising SEQ ID NO:2, SEQ ID NO:3, or SEQ ID NO:4, wherein the precursor fragment has a chocolate flavor when reacted with a reducing sugar.

2. The polypeptide of claim 1, wherein the flavor precursor fragment has an N-terminus comprising the sequence identified by SEQ ID NO:2, SEQ ID NO:3, or SEQ ID NO:4.

3. A chocolate flavored composition comprising the isolated polypeptide of claim 1.

4. A chocolate flavored composition comprising the isolated polypeptide of claim 2.

5. A chocolate flavored composition comprising a polypeptide identified by SEQ ID NO:2, SEQ ID NO:3, or SEQ ID NO:4.

6. The composition of claim 5, wherein the composition contains both the polypeptides identified by SEQ ID NO:2 and SEQ ID NO:3.

7. The composition of claim 5, wherein the composition contains a polypeptide identified by SEQ ID NO:4.

8. A polypeptide heterodimer comprising a first subunit having an amino acid sequence identified by SEQ ID NO:2, SEQ ID NO:3 or SEQ ID NO:4.

9. The polypeptide heterodinier of claim 8 wherein the first subunit is identified by SEQ ID NO:2.

10. The polypeptide heterodimer of claim 9, further comprising a second subunit identified by SEQ ID NO:3.

11. The polypeptide of claim 1 wherein the amino acid sequence is subjected to proteolytic degradation by an endopeptidase or in combination with an exopeptidase to obtain the chocolate flavor precursors.

12. A chocolate flavored composition comprising the isolated polypeptide of claim 11.

* * * * *

UNITED STATES PATENT AND TRADEMARK OFFICE
CERTIFICATE OF CORRECTION

PATENT NO. : 6,927,280 B2
DATED : August 9, 2005
INVENTOR(S) : Kochhar et al.

It is certified that error appears in the above-identified patent and that said Letters Patent is hereby corrected as shown below:

Column 14,
Line 25, change "heterodinier" to -- heterodimer --.

Signed and Sealed this

Eighteenth Day of October, 2005

JON W. DUDAS
*Director of the United States Patent and Trademark Office*